United States Patent [19]

Repensek et al.

[11] Patent Number: 4,844,102

[45] Date of Patent: Jul. 4, 1989

[54] IMPROVED NAIL COATING AND BONDING METHOD

[75] Inventors: William G. Repensek, Elm Grove, Wis.; Robert Blomquist, Elizabeth, N.J.

[73] Assignee: National Starch and Chemical Corporation, Bridgewater, N.J.

[21] Appl. No.: 142,386

[22] Filed: Jan. 11, 1988

[51] Int. Cl.⁴ .............................................. A45D 29/00
[52] U.S. Cl. ......................................... 132/73; 424/61
[58] Field of Search ..................... 132/73, 88.5, 88.7; 424/61

[56] References Cited

U.S. PATENT DOCUMENTS

| | | | |
|---|---|---|---|
| 3,564,078 | 2/1987 | Wicker et al. | 525/295 |
| 3,840,490 | 10/1984 | Gadzala et al. | 524/850 |
| 3,928,113 | 12/1975 | Rosenberg | 156/344 |
| 4,007,748 | 2/1977 | Matranga et al. | 132/73 |
| 4,222,399 | 9/1980 | Ionescue | 132/73 |
| 4,361,160 | 11/1982 | Bryce | 132/73 |
| 4,384,058 | 5/1983 | Galante | 524/32 |
| 4,407,310 | 10/1983 | Jadow | 132/73 |
| 4,450,848 | 5/1984 | Ferrigno | 132/73 |
| 4,552,160 | 11/1985 | Griggs | 132/73 |
| 4,612,444 | 9/1986 | Ragussa | 250/492.1 |
| 4,615,348 | 10/1986 | Nakata et al. | 132/73 |
| 4,626,428 | 12/1986 | Weisberg et al. | 424/61 |
| 4,627,453 | 12/1986 | Isler | 132/73 |
| 4,632,134 | 12/1986 | Reid | 132/73 |
| 4,641,669 | 2/1987 | Kimble | 132/73 |
| 4,646,765 | 3/1987 | Cooper et al. | 424/61 |
| 4,648,416 | 3/1987 | Kilman et al. | 132/73 |
| 4,669,491 | 6/1987 | Weisberg et al. | 132/73 |
| 4,687,827 | 8/1987 | Russo | 427/340 |
| 4,708,866 | 11/1987 | Turco et al. | 424/61 |

*Primary Examiner*—Gene Mancene
*Assistant Examiner*—Adriene J. Lepiane
*Attorney, Agent, or Firm*—Royal N. Ronning, Jr.; Edwin M. Szala

[57] ABSTRACT

This invention presents improved processes for applying artificial nails to natural fingernails and for applying durable protective coatings to the surface of natural nails. The improvements comprise applying a viscous cyanoacrylate adhesive to the nail surface and subsequently spreading the adhesive over the natural or combined artificial/natural nail surface using a solvent mixture containing a solvent capable of dissolving the adhesive and an effective amount of cyanoacrylate polymerization initiator. The use of this mixture permits easy spreading of the adhesive over the surface and causes polymerization of the cyanoacrylate on the surface. The result is a smooth coating over the entire surface to which polish can be applied.

14 Claims, No Drawings

IMPROVED NAIL COATING AND BONDING METHOD

BACKGROUND OF THE INVENTION

This invention relates to compositions and processes for applying artificial extensions to natural fingernails and/or for applying protective coatings to natural fingernails or toenails. More particularly, this invention relates to improved processes for attaching such artificial nail structures and coating natural nail surfaces which advantageously provides a smooth, durable coated surface upon which a conventional nail polish can be applied.

A wide array of artificial nail structures are available for attachment to natural nails (see, for example, U.S. Pat. No. 4,407,310 to Jadow, Oct. 4, 1983). Each of these structures has its own individual strengths and weaknesses, however two broad groups of artificial nails are observed to exist. In the first, the artificial nail structure covers substantially the entire surface of the natural nail to which it is attached. These type of structures suffer from the extreme drawback of preventing air from permeating into the natural nail bed, and thus require frequent removal (generally every 24–48 hours) to prevent damage to the natural nails. Additionally, such nails can serve as breeding stimulants for fungus infections, and, thus, the underlying nail bed must be kept scrupulously clean. Further, due to this lack of the natural nail "breathing" the user of such nail extensions may experience loss of normal touch sensation, and the ends of the nails may feel dead.

The second type of artificial nail consists of preformed nails which are applied to the outwardly extending edge of the natural nail, edge-to-edge with a slight overlap by means of various adhesives. When such nails are used, the application of the nail requires a substantial amount of manual dexterity, and additionally, the entire surface of both the natural and artificial nails must be coated with a substance which will "blend in", both nails and specifically avoid any appearance of a boundary joint between the two. Only after this boundary is smoothed, will the artificial extension appear as part of the natural nail.

A wide variety of techniques have been used to seal this joint. For example, in nail sculpting the clean nail is coated with a glue, usually a cyanoacrylate material which binds the artificial nail to the natural one. Then, a small brush is wetted with a liquid consisting of a blend of mono, di and trimethacrylate esters and a promoter, usually N,N-dimethyl-para-toluidine which is capable of inducing decomposition of benzoul peroxide at room temperature. The wetted brush is then dipped into a finely powdered polymethacrylate ester to form a dough which begins to cure immediately. The dough is quickly placed unto the prepared nails and smoothed or sculptured in place to cover the joint. More dough is added until the nail is covered and filled to the desired uniform thickness and shape. Filing, buffing and sometimes the addition of more dough result in a strong and durable surface to which polish can be applied. However, this system suffers from the drawback of requiring a wide array of materials, in addition to the cyanoacrylate adhesive which is originally used to bond the artificial nail to the natural nail, for proper use.

The use of cyanoacrylate itself as a filler has also been accomplished. In such a procedure the artificial nail is originally glued on to the tip of the natural nail by use of a cyanoacrylate glue. Once strong bonding is effected, the entire surface of the artificial and natural nail is coated with a viscous cyanoacrylate adhesive. This is accomplished in a three step process. Initially, the adhesive is applied to the nail surface. Subsequently, the adhesive is evenly spread across the surface by a solvent which is capable of dissolving the cyanoacrylate and is also readily evaporated at room temperature, to leave behind a smooth, even layer of cyanoacrylate. Finally, this layer is then cured by the application of an initiator, such as the dimethyl-para-toluidine, in a spray. This results in a hard, polymer-coated nail which can be polished; the joint is completely covered and hidden.

However, this procedure suffers from the drawback that the polymerization of the cyanoacrylate can be quite exothermic, and depending on the amount of promoter applied, quite high temperatures can be realized on the surface of the nail; these temperatures can cause great discomfort to the user. Additionally, the solvents normally used in spray applications, 1,1,1,-trichloroethylene, freons, and/or mixtures thereof, can cause potential problems when used in cosmetological applications since they may be potentially health hazards.

Thus, there exists a real need for a method of artificial nail application which will overcome these drawbacks. Such a procedure will provide for easy attachment and coating of said nails to achieve a natural and attractive appearance, not require great dexterity to attach the nails, and avoid the use of potentially hazardous solvents.

The same problems are observed when these fillers are used as protective coatings for natural fingernails or toenails (without the artificial extension). While it is desirable to achieve a tough, smooth, and resilient coating on the nail surface, these drawbacks limit the utility of the fillers in this regard. Thus, there exists a real need for a method for coating natural nails which overcomes these drawbacks.

SUMMARY OF INVENTION

It is an object of this invention to present a method for the attachment of artificial nails to a natural nail which permits the artificial nail to be blended in and contoured with the surface of the natural nail. It is further an object of this invention to provide a quick, one-step, process for applying such nails which overcomes the problems of the spray applied initiators of the prior art. It is also an object of this invention to provide a method for coating natural nails which provides a smooth resilient coating that overcomes these same problems.

In one embodiment, this invention presents an improved method of bonding an artificial nail to a natural nail. In the initial steps the sculptured artificial nail (generally) made of ABS or nylon) is adhesively bonded to the tip of the natural nail by a cyanoacrylate adhesive. Once this adhesive is set, the desired amount of a cyanoacrylate adhesive is applied to the center of the natural nail and then spread evenly over the surface of both nails using a brush wetted with the solvent capable of dissolving the cyanoacrylate adhesive. This solvent also contains, dissolved within it, an effective amount of a polymerization initiator, which causes polymerization of the cyanoacrylate and results in a hard, durable coating over the surface of the nail. The application of the initiator concurrent with the solvent grants the additional benefit of limiting the magnitude of the exotherm observed during the polymerization of the cyanoacrylate, since the evaporation of the solvent will remove heat from the entire system thereby providing a cooling effect. Thus the user of such a system will experience a far lower temperature increase on the surface of the nail than with any other initiator application method.

Additionally, the solvent can be chosen to avoid exposure to toxic and/or dangerous solvents used in the prior art wherein the initiator was applied in an aerosol spray. In this manner, the invention presents a safe and simple method for the application and attachment of artificial nails to natural nail beds.

In another embodiment of this invention this same cyanoacrylate is used as a coating which fills the natural ridges and any imperfections on the surface of natural fingernails and toenails, providing a tough, smooth resilient coating to which polish can be applied.

DETAILED DESCRIPTION OF INVENTION

In its first embodiment, this invention presents an improved method for bonding and sculpting artificial fingernails to natural fingernails to result in a smooth and attractive surface to which fingernail polish can be applied. The resultant artificial/natural fingernail composite, once coated with polish, appears natural and is durable and smooth.

In the method of this invention, the composite is achieved in three steps. Initially, the artificial fingernail is bonded to the natural nail, using a cyanoacrylate adhesive. While the preferred artificial nail is a tip which is applied at the tip of the natural fingernail, with only a slight overlap, it can be applied in virtually any position on the fingernail. Use of an adhesive is preferred due to its quick setting time and strong ultimate bond strength, but the inventors contemplate that virtually any adhesive can be employed in this step, the only criterion for choice being the compatibility of the adhesive with the cyanoacrylate used as a coating agent.

Once the above adhesive has set and the artificial fingernail is cemented firmly in place, a viscous cyanoacrylate adhesive is applied directly to the surface of the artificial/natural fingernail composite. This adhesive, which may be the same as, or different from the cyanoacrylate adhesive used in the first step, must be of a sufficient viscosity to prevent its flow across the fingernail composite surface, yet not so viscous as to prevent its convenient application. To achieve this viscosity, it is preferred that the solvent content of this adhesive be kept as low as practical; however, adhesives containing a wide range of solvent concentrations can be employed. Some suitable adhesives are PB 102 (containing 5.8% Cab-O-Sil) and PB-200.

The final step in the method of this invention is the spreading and curing of the viscous cyanoacrylate adhesive. This is accomplished by using a solvent mixture which contains both a solvent capable of dissolving the cyanoacrylate and an initiator capable of causing the cyanoacrylate to polymerize (or cure). In this single step, the solvent mixture is applied, by brushing or other convenient means, directly to the surface of the viscous cyanoacrylate adhesive. The solvent acts to reduce the viscosity of the adhesive, permitting it to be spread evenly and smoothly over the entire surface of the composite, while the initiator causes the acrylate to polymerize without the use of heat and/or pressure. The result is a smooth, natural-appearing surface exhibiting no visible demarcation or boundary between the artificial and natural fingernail surfaces. The cured adhesive is, however, removable using any cyanoacrylate remover.

The use of this one step process also confers the added benefit of maintaining control over the magnitude of any temperature increase realized on the fingernail surface. Since the polymerization of cyanoacrylate is exothermic, a major problem with previous systems using cyanoacrylate was the temperatures realized on the nail surface, which could cause considerable discomfort to the user. In the method of the instant invention the polymerization occur in the presence of a solvent which is evaporated during the process; since this evaporation removes heat from the system, by proper choice of solvent, the temperature increase realized on the nail surface can be kept to a minimum.

Further, by proper choice of application means, the solvent mixture can be applied directly to the nail, avoiding contacting it with any surrounding skin surfaces; this non-directability is a major problem with the aerosol method currently used for applying the initiator in some systems. In the method of the instant invention, the preferred application means is by brushing, but any other means such as transfer by pipette, dropping from a solid glass rod, applying by cotton or tissue, etc. can be used, with the only criterion being the ability of the system to permit the user of the system to control the precise location to which the solvent mixture is applied.

Additionally, since the solvent used for smoothing and spreading the cyanoacrylate is also used for applying the initiator, the method of the instant invention permits the user to avoid exposure to the potentially dangerous solvents, such as 1,1,1-trichloroethylene and the freons, which are used in the aerosol application method currently employed. By proper choice of solvent, the danger to the user can be minimized.

In the instant invention, virtually any solvent capable of dissolving both the cyanoacrylate adhesive and the initiator can be employed in the solvent mixture. However, since the solvent will be applied as a cosmetic, it must be chosen from materials which are physiologically compatible and free of health risks. One solvent meeting these criteria is ethyl acetate, a solvent used in many nail polishes currently being sold.

The initiator used in the solvent mixtures must also be of a minimal health risk, yet capable of catalyzing the polymerization of the cyanoacrylate. Additionally, since such materials are expensive it must be capable of being effective at a low concentration in the mixture; preferably less than 2% (by weight), more preferably ranging from 0.001 to 1% (by weight, most preferably 0.01-0.5% (by weight). One such initiator is N-N-dimethyl-p-toluidene (DMPT). It has been found that when ethyl acetate is the solvent, 0.1-0.2% (by weight) of DMPT will act satisfactorily, and concentrations as low as 0.05% will produce a cure. Further, if the solvent used is free of impurities (i.e. reagent grade), amounts of DMPT as low as 0.009% will produce a satisfactory cure time and finish.

In the second embodiment, this invention presents a method for applying a protective coating to the surface of natural fingernails and toenails. In this method, the viscous cyanoacrylate adhesive is placed directly onto the surface of the natural nail and then smoothed using the solvent mixture containing the initiator as described supra; except for the absence of the artificial nail, this method is identical to the method for bonding artificial nails, and the same solvents and initiators can be used. The cyanoacrylate acts to fill the natural ridges and any imperfections in the nail surface and, once cured, presents a durable, smooth, and resilient coating to which nail polish can be applied.

The cured coating will last for an extended period of time, often a month or more, and acts to protect the nail from damage due to scratching or other abrasions. Further, because the coating is acrylate-based, it will tend to bond acrylic nail polishes more tightly resulting in a longer lifetime for the polish.

EXAMPLES

To assess the curing times of cyanoacrylate when treated as described in the methods of the instant invention, three cyanoacrylate formulations were used.
1. A mixture of 423.9 gm PB102 (a proprietary cyanoacrylate adhesive) and 26.1 gm Cab-O-Sil
2. Super Nail No lite Gel
3. Gena & Pro-Gel (Gena Laboratories)

The two latter materials are available commercially and are cured by the spray method described supra.

Three solutions of initiator (N,N-Dimethyl-p-Toluidine) in standard grade ethyl acetate were prepared:
A. 0.1% (by weight) initiator
B. 0.05% (by weight) initiator
C. 0.2% (by weight) initiator In the first experimental series the cyanoacrylate formulation was applied to the surface of artificial nails and, immediately thereafter, the initiator/ethyl acetate solution was applied and the cyanoacrylate was spread across the entire surface; the time required for the subsequent curing of the composition was then measured. The results are presented in Table I:

TABLE I

| Trial | Form. No. | Solution | Time to Cure |
|---|---|---|---|
| 1 | 2 | A | <1 min. |
| 2 | 3 | A | <1 min. |
| 3 | 2 | B | >2 min. |
| 4 | 3 | B | 1 min., 15 sec. |
| 5 | 2 | C | 45 sec. |
| 6 | 3 | C | 15 sec. |
| 7 | 1 | A | 45 sec. |
| 8 | 1 | B | 2 min. |
| 9 | 1 | C | 30 sec. |

The results indicate the solutions A and C promote curing in less than 1 minute. In a second set of experiments, a viscous proprietary cyanoacrylate, PB200, was applied to the surface of natural nails, and then spread and examined as described above. The surfaces were then physically examined for finish appearance. Some blotchy or uneven surfaces were cleaned with acetone and subsequently observed.

TABLE II

| Trial | Solution | Time to Cure | Physical Observation |
|---|---|---|---|
| 1 | A | 45 sec. | smooth, high gloss surface |
| 2 | B | 30 sec. | blotchy, high gloss surface, after acetone, surface was smooth to touch, but still blotchy |
| 3 | C | 10 sec. | smooth, high gloss surface |
| 4 | B | — | uneven, blotchy surface which remained the same |
| 5 | A | 30 sec. | blotchy, high gloss surface |

The results reveal that solution C (0.2% initiator) presents the fastest cure time and highest quality cured surface. Further, acetone does not appear to affect the surface.

A third solution of initiator, 0.009% N-N-DMPT in reagent grade ethyl acetate (solution D) was then prepared and compared to solution C for its ability to cure PB200 on a variety of surfaces, using the above application methods. The results are summarized in Table III.

TABLE III

| Trial | Solution | Surface | Time to Cure | Physical Observation |
|---|---|---|---|---|
| 1 | D | Glass | 7 min. 40 sec. | — |
| 2 | C | Glass | 2 min. 15 sec. | — |
| 3 | D | Delrin Acetal 500 | 55–60 sec. | Clear and smooth |
| 4 | C | Delrin Acetal 500 | 15–20 sec. | Clear and smooth |
| 5 | D | Human fingernail | 45–50 sec. | Clear and smooth |
| 6 | C | Human fingernail | 10–15 sec. | Clear and smooth |

Thus, it appears that the use of a pure solvent will lower the amount of initiator required for satisfactory curing times.

It is apparent that many modifications and variations of this invention as hereinabove set forth may be made without departing from the spirit and scope thereof. The specific embodiments described are given by way of example only and the invention is limited only by the terms of the appended claims.

What is claimed is:
1. An improved method for applying artificial fingernails to natural fingernails wherein the improvement comprises:
   (a) bonding said artificial fingernail to said natural fingernail using an adhesive;
   (b) subsequently applying to said natural fingernail a viscous cyanoacrylate adhesive in an amount sufficient to achieve coating of the entire combined surface of the natural and artificial fingernails; and
   (c) shortly thereafter applying to said viscous cyanoacrylate adhesive a solvent mixture and spreading the solvent mixture and adhesive over the surface of the artificial and natural fingernails such that the cyanoacrylate is evenly spread over said surface, wherein said solvent mixture comprises a solvent capable of dissolving the viscous cyanoacrylate adhesive and an effective amount of a cyanoacrylate polymerization initiator such that the cyanoacrylate is polymerized o said surface.

2. The method of claim 1, wherein the adhesive is a cyanoacrylate adhesive.

3. The method of claim 1, wherein the solvent is ethyl acetate.

4. The method of claim 1, wherein the polymerization initiator is N-N-dimethyl-p-toluidene.

5. The method of claim 1, wherein the solvent mixture is ethyl acetate containing from 0.05-0.2%, by weight, N-N-dimethyl-p-toluidene.

6. The method of claim 1, wherein the solvent mixture is ethyl acetate containing 0.2%, by weight, N-N-dimethyl-p-toluidene.

7. The method of claim 1, wherein the solvent mixture comprises 0.009%, by weight, N-N-dimethyl-p-toluidine in reagent grade ethyl acetate.

8. The method of claim 1, wherein the artificial nail is bonded to the tip of the natural fingernail.

9. An improved method for protecting and strengthening natural fingernails and toenails wherein the improvement comprises:
   (a) applying to said natural fingernail or toenail a viscous cyanoacrylate adhesive in an amount sufficient to achieve coating of the entire surface of the nail; and
   (b) shortly thereafter applying to said viscous cyanoacrylate adhesive a solvent mixture and spreading the solvent mixture and adhesive over the surface of the natural fingernail or toenail such that the cyanoacrylate is evenly spread over said surface, wherein said solvent mixture comprises a solvent capable of dissolving the viscous cyanoacrylate adhesive and an effective amount of a cyanoacrylate polymerization initiator such that the cyanoacrylate is polymerized on said surface, forming a durable, resilient, and smooth coating.

10. The method of claim 9, wherein the solvent is ethyl acetate.

11. The method of claim 9, wherein the polymerization initiator is N-N-dimethyl-p-toluidene.

12. The method of claim 9, wherein the solvent mixture is ethyl acetate containing from 0.05–0.2%, by weight, N-N-dimethyl-p-toluidene.

13. The method of claim 9, wherein the solvent mixture is ethyl acetate containing 0.2%, by weight, N-N-dimethyl-p-toluidene.

14. The method of claim 9, wherein the solvent mixture comprises 0.009%, by weight, N-N-dimethyl-p-toluidine in reagent grade ethyl acetate.

* * * * *